(12) United States Patent
Knecht

(10) Patent No.: US 7,918,812 B2
(45) Date of Patent: Apr. 5, 2011

(54) COMPRESSION-SUSPENSION STRAP ASSEMBLY AND KNEE BRACE EQUIPPED THEREWITH

(75) Inventor: Steven S. Knecht, Bakersfield, CA (US)

(73) Assignee: Townsend Industries, Inc., Bakersfield, CA (US)

( * ) Notice: Subject to any disclaimer, the term of this patent is extended or adjusted under 35 U.S.C. 154(b) by 226 days.

(21) Appl. No.: 12/274,507

(22) Filed: Nov. 20, 2008

(65) Prior Publication Data
US 2010/0125231 A1    May 20, 2010

(51) Int. Cl.
*A61F 5/00* (2006.01)
*A61F 5/37* (2006.01)
(52) U.S. Cl. .................. 602/26; 602/5; 602/23; 128/888
(58) Field of Classification Search .................. 128/882; 602/5, 16, 20, 23, 24, 25, 26, 27, 28, 29, 602/60, 61, 62, 65
See application file for complete search history.

(56) References Cited

U.S. PATENT DOCUMENTS

| 4,854,308 | A | | 8/1989 | Drillio | |
|---|---|---|---|---|---|
| 4,940,045 | A | | 7/1990 | Cromartie | |
| 5,288,287 | A | * | 2/1994 | Castillo et al. | 602/16 |
| 5,472,412 | A | * | 12/1995 | Knoth | 602/26 |
| 5,857,989 | A | | 1/1999 | Smith, III | |
| 6,740,054 | B2 | | 5/2004 | Stearns | |
| 7,311,687 | B2 | * | 12/2007 | Hoffmeier et al. | 602/26 |
| 2007/0063459 | A1 | * | 3/2007 | Kavarsky | 280/14.23 |

* cited by examiner

*Primary Examiner* — Patricia M Bianco
*Assistant Examiner* — Ophelia Hawthorne
(74) *Attorney, Agent, or Firm* — Roberts Mlotkowski Safran & Cole, P.C.; David S. Safran

(57) ABSTRACT

A knee brace is provided with semi-pliable inserts affixed to inner sides of femoral links of the brace at two points with a bottom portion of the insert left free to move inward toward a facing side of the leg. Anterior and posterior straps that are tightenable by the wearer are attached to the semi pliable inserts in a manner enabling pulling on the straps to cause the inserts to dynamically move inward and compress against the thigh so as improve comfort by diffusing and transferring pressure away from a relatively boney side of the knee of the wearer to a softer thigh area of the wearer. The inserts are also adapted to move inward and press into femoral hollows just proximal to the knee joint of the wearer so as to provide support against movement of the brace along the length of the leg of the wearer.

17 Claims, 8 Drawing Sheets

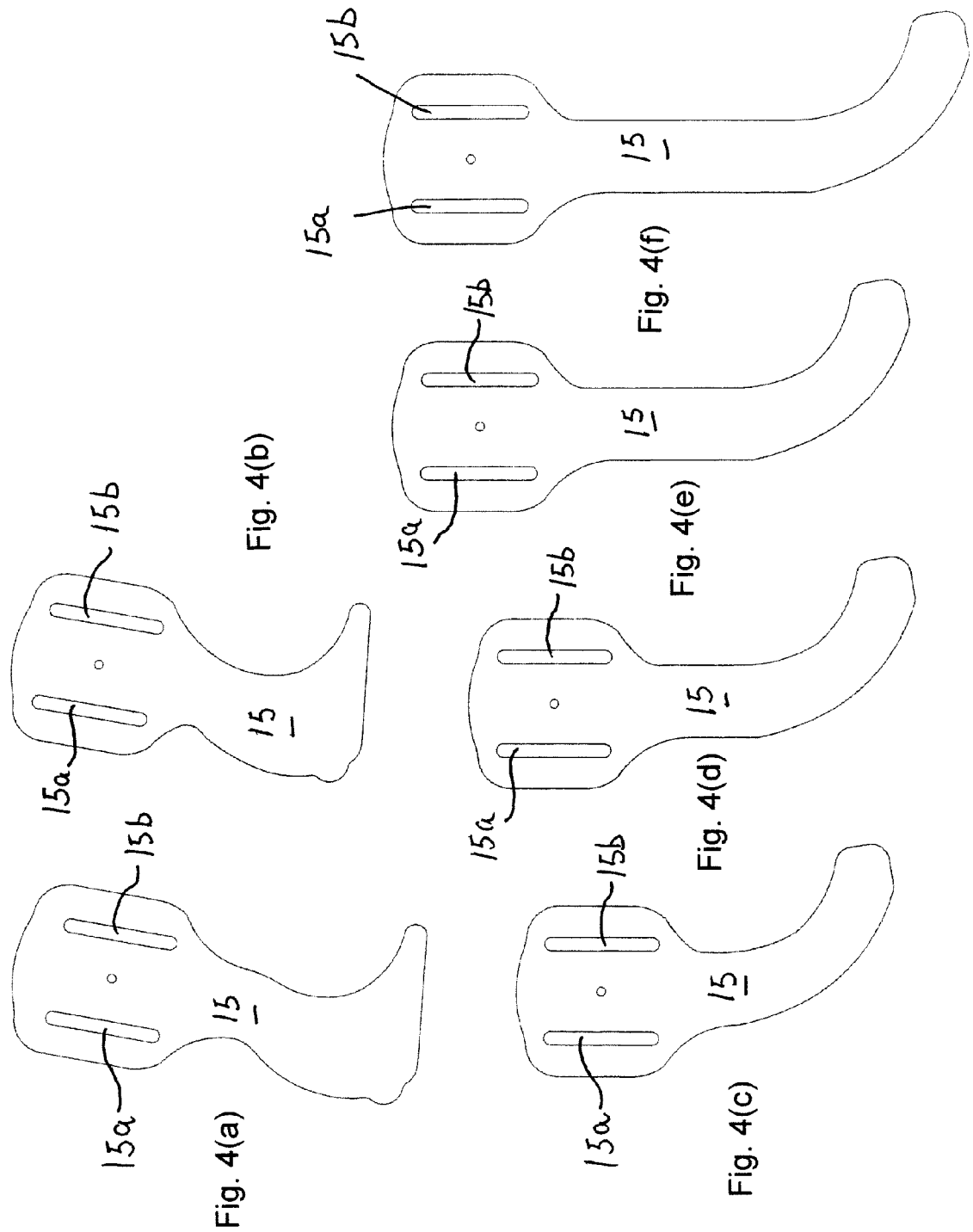

COMPRESSION-SUSPENSION STRAP ASSEMBLY AND KNEE BRACE EQUIPPED THEREWITH

BACKGROUND OF THE INVENTION

1. Field of the Invention

The present invention relates to knee braces, and in particular, osteoarthritis (OA) knee braces and other types of braces which provide protection and support for injuries and instabilities.

2. Description of Prior Art

A prior concept initiated by Gregg Berretta, CPO, that he called a "T-Force Strap" involved adding of a single pad pivotally attached above the condyle pad on commercially available osteoarthritis (OA) knee braces and that could be tightened against the wearer's leg by a strap connect to the pad. The purpose of the "T-Force Strap" was to diffuse the corrective forces produced by the brace so that all of the pressure would not be concentrated on the condyle of the wearer so as to make the brace more comfortable and resulted in higher patient compliance.

Hoffmeir et al. U.S. Pat. No. 7,311,687 shows another arrangement designed to distribute loads over a large portion of the wearer's leg and otherwise improve fitting of an osteoarthritis brace on a wearer's leg. In this case, a semi-rigid cuff is attached in the middle of a rigid thigh cuff and as this inner cuff is tightened around the thigh, it moves away from the rigid cuff and is intended to bear reaction forces created by a medial/lateral force applied to the wearer's knee by the hinge of the brace.

Stearns U.S. Pat. No. 6,740,054 discloses an orthopedic brace assembly having a suspension assembly with a pair of cantilevered arms. Each of the arms is connected to a respective one of the femoral arms of the brace just above the hinge and extends toward the other of the cantilevered arms. A dome-shaped pad is mounted on the free ends of the cantilevered arms and the free ends are connected by an elastic strap. The stated purposes of the elastically-connected cantilevered arms being to control the tibial by providing translational and rotational stability otherwise provided by a normally functioning anterior cruciate ligament (ACL) and to limit migration of the brace during knee articulation.

No known knee brace has a single assembly that is able to both improve the comfort of the brace by distributing the corrective forces produced by the brace and at the same time is able to produce a suspension effect that inhibits migration of the brace during flexion and extension of the leg wearing the brace.

SUMMARY OF THE INVENTION

In view of the foregoing, it is an object of the present invention to improve the comfort for the wearer of a knee brace by providing an arrangement that is capable of both distributing the corrective forces produced by the brace, and at the same time, producing a suspension effect that inhibits migration of the brace during flexion and extension of the leg wearing the brace.

These objects are achieved by a compression-suspension strap assembly having straps that are not connected directly to the rigid outer shell of the brace, but rather the straps are positioned just above the knee and are attached to semi-pliable inserts. An anterior strap has a point of origin and attachment on one side of the brace and stretches across the front of the thigh and through a slot on the opposing insert, and a posterior strap is similarly attached to one side of the brace and crosses the back side of the leg to fit through the slot in the opposing insert. When the anterior and posterior straps are tightened, the attachment through the slots draws the inserts inward to provide dynamic compression against the sides of the leg above the knee.

Two specific functional results are produced by the dynamic pressure applied to the leg. The first relates to brace suspension, which involves the use of compression to counter gravitational forces that may cause the brace to move in a downward direction on the leg (brace migration) due to the conical shape of the leg (i.e., large thigh over a smaller sized knee and calf). The second relates to the diffusion and transference of pressure away from the side of the knee (a more bony aspect of the leg) to the softer and more cushioned thigh area. This is particularly applicable to braces that are designed to apply corrective forces to the limb, with pressure typically centered on the side of the knee. Dynamic pressure applied just about the knee, by the semi-pliable inserts, enhances the delivery of corrective forces in a manner that is more comfortable and tolerable for the user.

These and other features and advantages of the present invention will become apparent from the following detailed description in conjunction with the accompanying drawings.

BRIEF DESCRIPTION OF THE DRAWINGS

FIGS. 4(a)-4(h) show examples of various configurations for semi-pliable inserts of the compression-suspension strap assembly that is shown in FIGS. 1-3 with FIGS. 4(g) & 4(h) showing an alternative strap attachment.

DETAILED DESCRIPTION OF THE INVENTION

Figure 1:
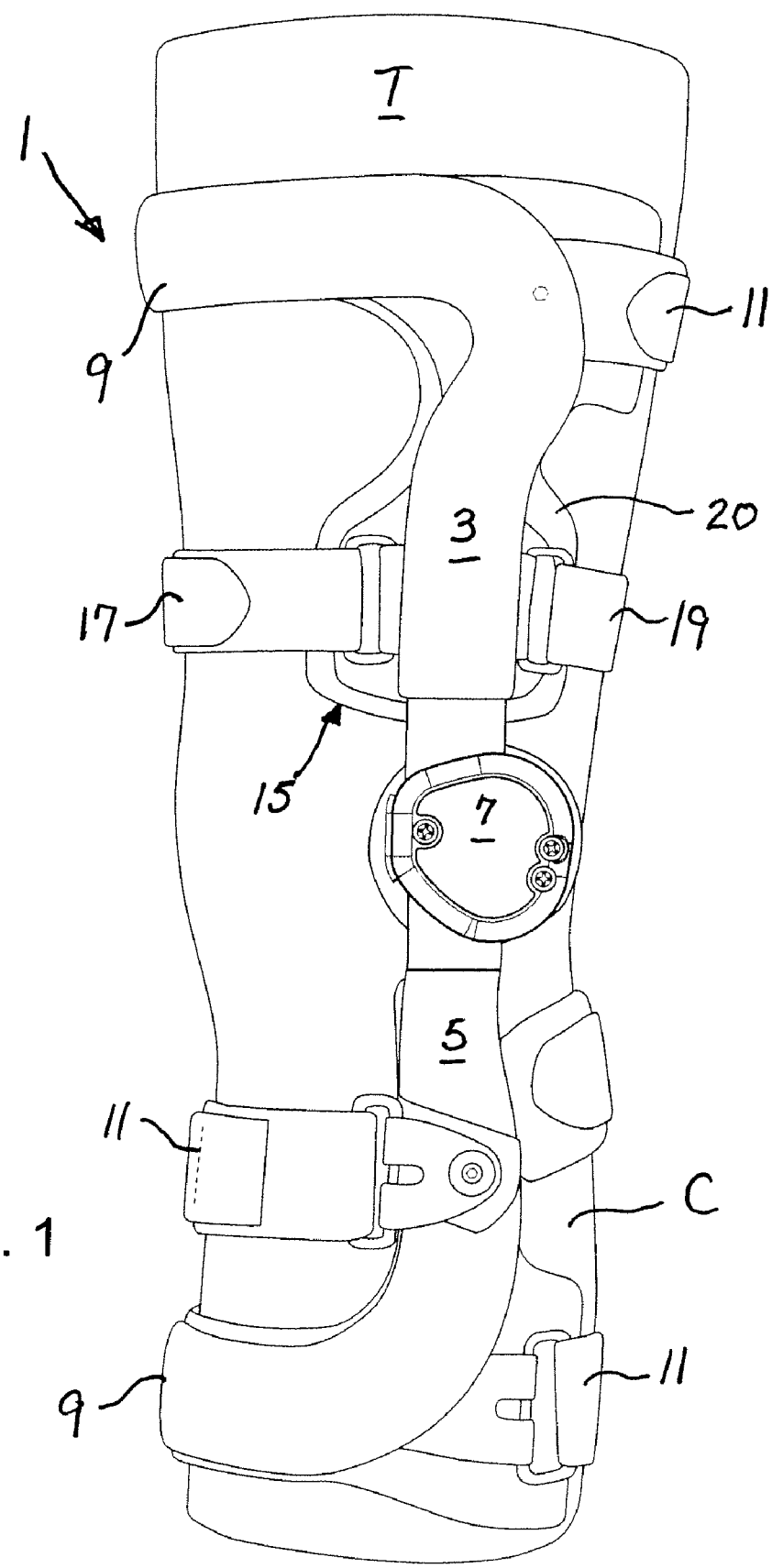
FIG. 1 is a left side elevational view of a knee brace with compression-suspension strap assembly in accordance with the present invention.
Figure 2:
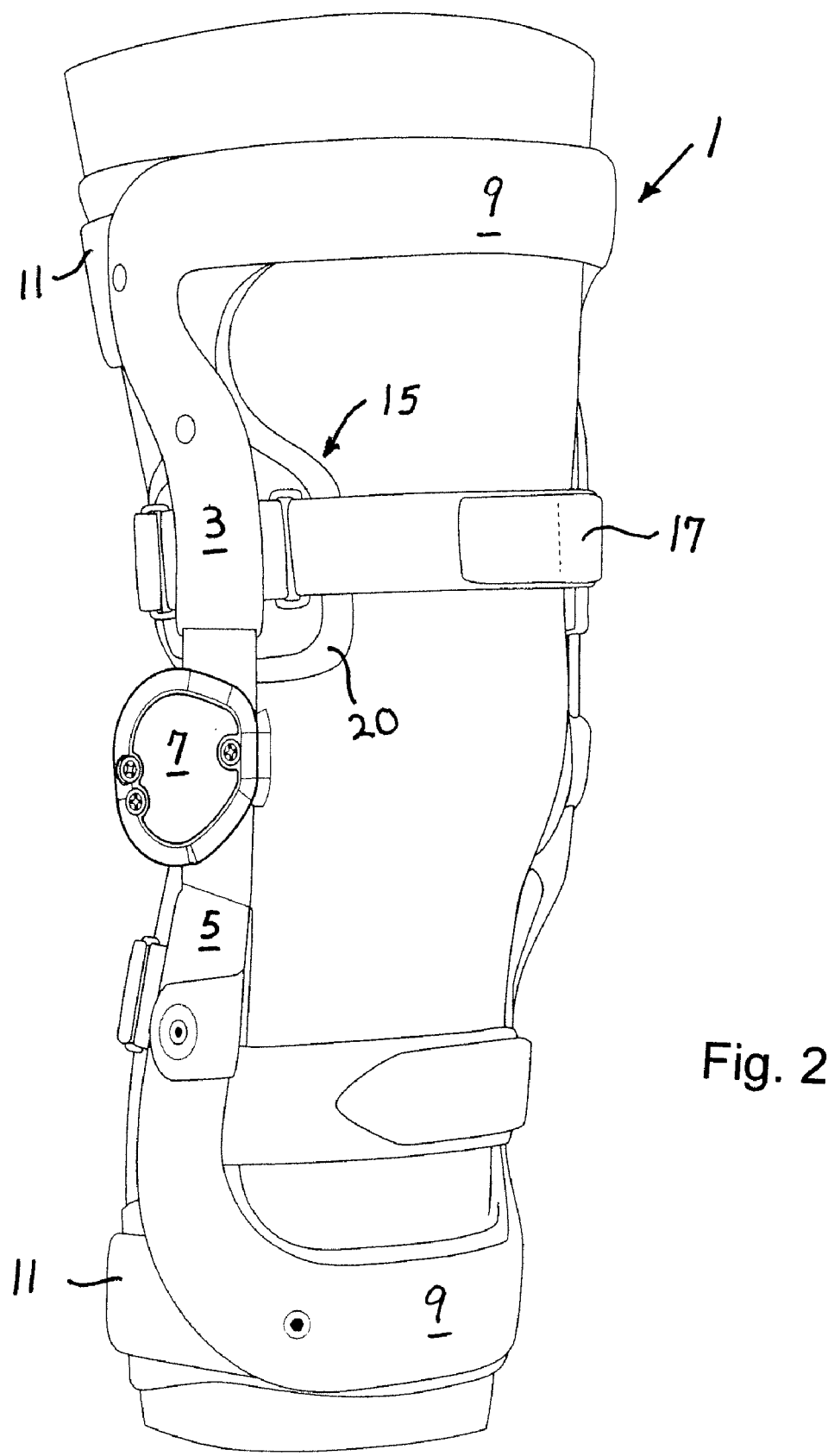
FIG. 2 is a right-front perspective view of the knee brace shown in FIG. 1.
Figure 3:
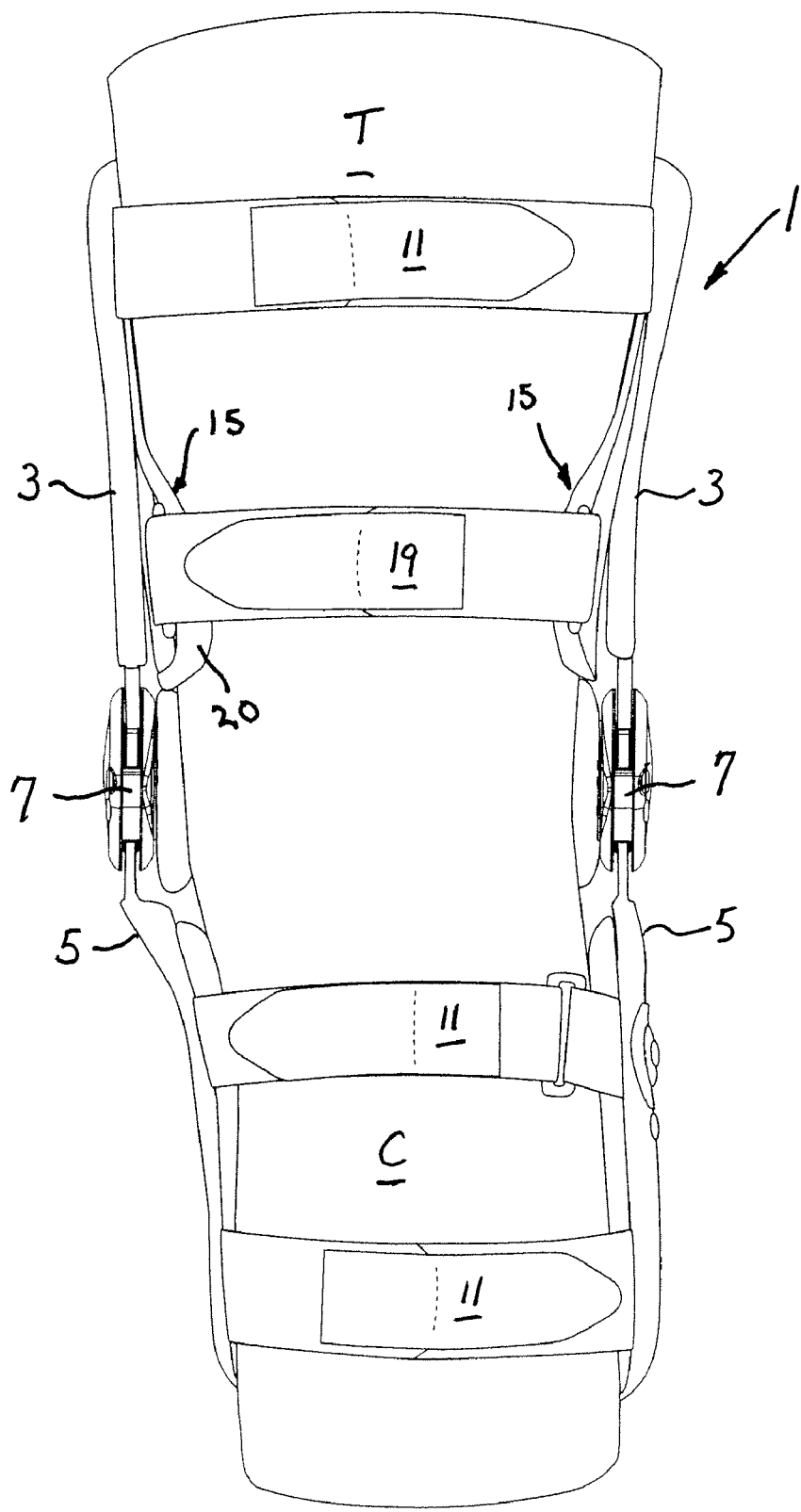
FIG. 3 is a rear elevational view of the knee brace shown in FIG. 1.

The basic components of the knee brace 1 can be of any conventional design, such as those of U.S. Pat. Nos. 6,981,957; 6,500,139; 6,413,232; 5,743,865; 5,259,832, all of which are owned by the assignee of the present application, as well as those of other manufacturers of knee braces, particularly osteoarthritis (OA) knee braces. With reference to FIGS. 1-3, typical knee braces of the type to which the invention finds applicability have a pair of rigid, upper, femoral struts 3 that are connected to a pair of rigid, lower, tibial struts 5 via a hinge joint 7. Furthermore, the femoral struts 7 are connected to each other by a rigid cross brace 9 and the same is true for the tibial struts 5. Additionally, at least one strap 11 fixes the brace on the thigh T of the leg of the wearer and at least one strap 11 fixes the brace on the calf C of the leg of the wearer.

In accordance with the invention, a semi-pliable insert 15 is affixed to the inner side of the femoral strut 3 on the medial side, and a second insert 17 is affixed to femoral strut 3 on the lateral side. There are two points of fixation on each side, the first being at the proximal (top) end of the insert 15, and the second being approximately at the middle of the insert 15 so that the distal (bottom) portion of the insert is free to move inward toward the side of the leg.

Unlike the other straps on the brace that connect directly to the rigid outer shell, e.g., straps 11, the two straps 17, 19 are positioned just above the knee and are attached to the semi-pliable inserts 15 and not the rigid elements of the brace itself. In particular, there are two vertical slots 15*a*, 15*b* cut into the lower portion of each insert 15. These slots 15*a*, 15*b* accommodate transverse anterior and posterior straps 17, 19 that can be tightened by the patient. Each of the straps 17, 19 are attached in a respective one of the slots 15*a*, 15*b* of one of the inserts 15 and is inserted through the respective slot 15*a*, 15*b* in the other of the semi-pliable inserts 15 to run back to a point of attachment on an initial portion of the strap, the strap end being securable on the initial portion, e.g., via a VELCRO® hook and loop type closure.

Figures 4G, 4H:
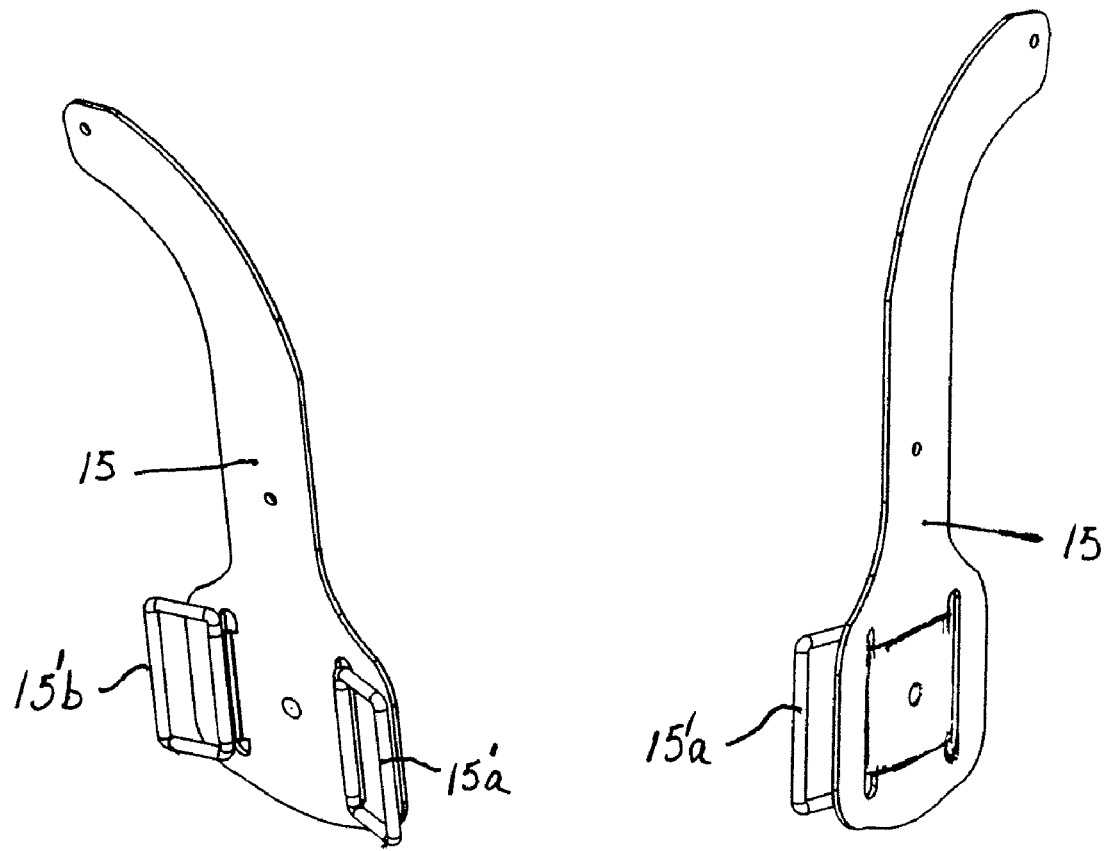

However, preferably, a pair of metal rings or loops 15'*a*, 15'*b* (FIGS. 4(*g*) & 4(*h*)) are attached to the rear of the inserts 15, e.g., by rivets, and the straps 17,19 pass freely through these rings or loops 15'*a*, 15'*b* instead of through slots in the inserts themselves. Such rings or loops 15'*a*, 15'*b* would have greater strength than the plastic of the inserts 15 and the straps will pass more smoothly and with less wear through metal rings or loops than across the plastic edge of a slot 15*a*, 15*b* in the inserts 15.

The direction of pull and the collaborative use of both the anterior positioned strap 19 running across the back of the thigh and the posterior positioned strap 17 running across the front of the thigh cause the inserts to dynamically move inward and compress against the thigh T when the straps 17, 19 are independently tightened by the user.

There are two specific functional results produced by this dynamic pressure being applied to the limb. The first relates to brace suspension, which involves the use of compression to counter gravitational forces that may cause the braces to move in a downward direction on the limb (brace migration) due to the conical shape of the leg (i.e., large thigh over a smaller sized knee and calf). The second relates to the diffusion and transference of pressure away from the side of the knee (a more bony aspect of the leg), to the softer and more cushioned thigh area. This is particularly applicable to braces that are designed to produce corrective forces to the limb, with pressure typically centered on the side of the knee. Dynamic pressure applied just about the knee, by the semi-pliable inserts 15, enhances the delivery of corrective forces in a manner that is more comfortable and tolerable for the user.

Pads 20 are attached to the interior side of the semi-pliable inserts 15 so that there is a comfortable interface between the plastic of the inserts and the user's skin. These pads 20 perform no function other than to prevent skin irritation or discomfort when the straps are tightened and the inserts move inward and press into the tissues above the knee that can generally be described as the femoral hollows just proximal to the knee joint. There are also pads (not shown) attached to the interior side of the straps that provide a soft interface that also serve to prevent skin irritation and enhance user comfort.

As shown in FIGS. 4(*a*)-4(*f*), the inserts 15 can be of various lengths and have a generally hook-shaped upper portion, i.e., the portion at which the insert 15 is attached to rigid body of the brace. It is possible to use inserts 15 of differing lengths, in which case the insert 15 that extends down to the side of the knee that is opposite that which has the compartment that is compromised would be the longer pad to distribute corrective force over a broader segment of the leg and to lessen the concentration of force on the bony side of the knee thereby improving comfort and reducing the potential for irritation. The second, shorter insert 15 would be sized to terminate above the affected compartment to compress into the soft tissue of the femoral hollow proximal to the knee to help prevent brace migration.

However, it has been found to normally be preferable to use a pair of inserts 15 that are of the same length, in which case both would be inserts would be of the shorter type just described. In this regard, it is noted that, while it has been indicated that the present invention finds particular applicability to osteoarthritis knee braces, the invention will also find applicability in many other situations, such as on ligament functional instability knee braces where the use of two of the shorter type of inserts can be advantageous for providing dynamic compression and suspension.

As also reflected by FIGS. 4(*a*) to 4(*f*), no one insert length/configuration will be best for all patients so that a particular insert should be selected based on the size and shape of the leg of the individual to be lifted with the brace as well as the reason that the brace has been prescribed.

Figures 5, 6A, 6B, 6C:
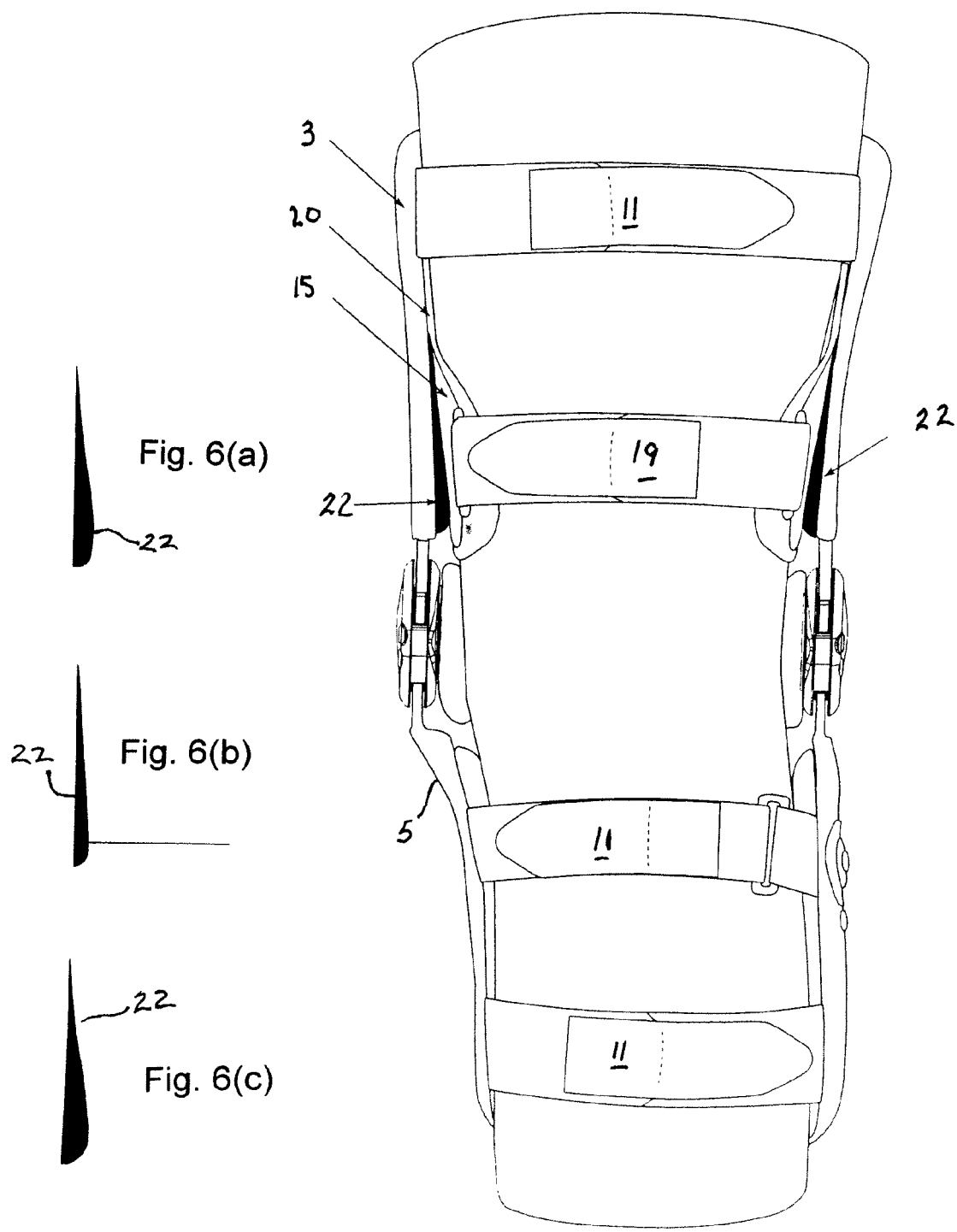
FIG. 5 is a rear view of a knee brace as shown in FIGS. 1-3 to which wedges or bladders have been added.
FIGS. 6(a)-6(c) show examples of various configurations for wedges or bladders for use as shown in FIG. 5.

FIG. 5 and FIGS. 6(*a*) to 6(*c*), show the use of rigid or semi-rigid wedges 22 placed between the inserts 15 and the femoral strut 3 to create compression. While the wedges 22 are shown on both the medial and lateral sides in FIG. 5, a singe wedge 22 can be used on one or the other side of the brace as needed. As shown by FIGS. 6(*a*) to 6(*c*), wedges of different thickness can be utilized to obtain greater or lesser degrees of compression. Alternatively, the wedges could be pneumatic bladders that achieve greater or lesser degrees of compression depending on the degree to which they are pressurized.

Figure 7:
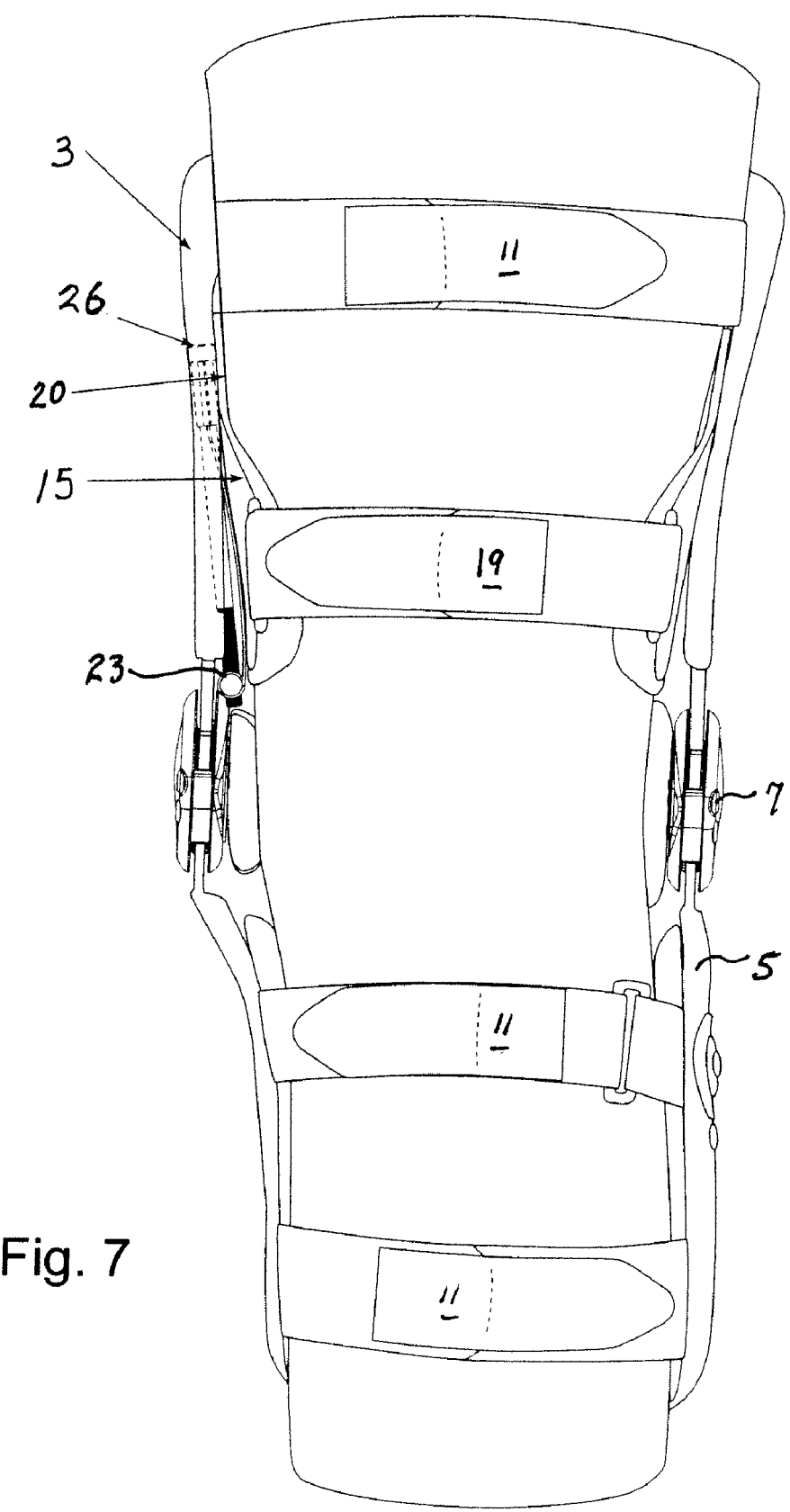
FIG. 7 is a rear view of a knee brace as shown in FIGS. 1-3 to which screw jack type wedges have been added.
Figure 8A:
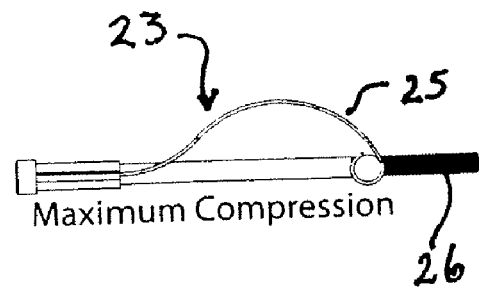
FIGS. 8(a) & 8(b) are side and perspective views of the screw jack type wedge shown in FIG. 7 in a maximum compression position.
Figure 8B:
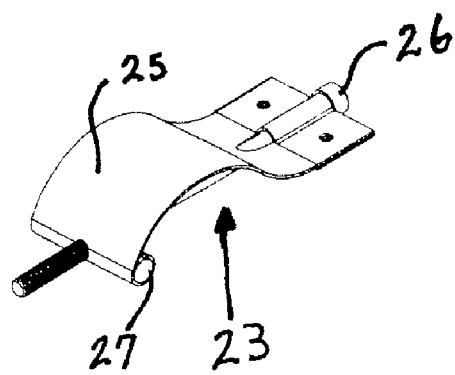
Figure 9A:
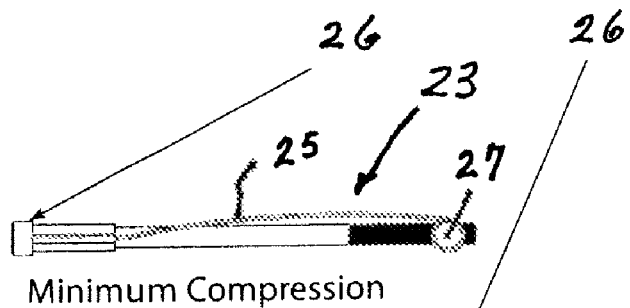
FIGS. 9(a) & 9(b) are side and perspective views of the screw jack type wedge shown in FIG. 7 in a minimum compression position.
Figure 9B:
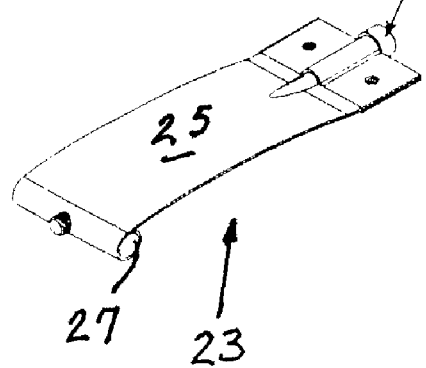

Yet another means for creating varying degrees of compress is shown in FIGS. 7, 8(*a*), 8(*b*), 9(*a*) and 9(*b*). In this case, a screw jack wedge 23 is formed by a spring plate 25 and a screw jack formed of a bolt 26 and draw rod 27. On end of the spring plate 25 is attached to the shank of the bolt 26 and the other to the draw rod 27 as shown in FIGS. 8(*a*), 8(*b*), 9(*a*) and 9(*b*). The threaded end of the bolt 26 is threaded into the draw rod 27. Tightening of the bolt 26 into the draw rod 27 forces the spring plate 25 to bow, thereby causing the insert 15 to move inward toward the leg of the wearer. FIGS. 8(*a*) and 8(*b*) show the screw jack wedge 23 in a state for causing maximum compression while FIGS. 9(*a*) and 9(*b*) show the screw jack wedge 23 in a state for causing minimum compression and corresponds to the state shown in FIG. 7.

It should be appreciated that other mechanisms than those described for pushing or holding the insert 15 inward against the leg of the wearer are also possible. Thus, the above described wedges should only be viewed as representative examples of techniques that can be used. Furthermore, the use of such wedges, while shown as being supplemental to the use of the straps 17, 19, in some cases could be used without such straps, in which case some form of disengageable connection between the wedge and plastic of the insert, such as a pin on the wedge that engages in a recess in the outer side of the insert, is suggested to stabilize the posterior-anterior position of the insert 15 that would otherwise be achieved by the action of the straps 17, 19.

It is also pointed out that, while the use of two semi-pliable inserts 15 with two separate straps 17, 19, as shown is preferred, it is also possible to use a single strap arrangement. That is, for osteoarthritis correction, a single strap can be fixed to one of the femoral struts 3 and threaded through the insert 15 on the opposite strut 3. The insert 15 on the side at which the single strap is fixed would then also be fixed. Tightening of the single strap acts to pull the leg toward the fixed insert. This would be effective for transferring some of the corrective force from the side of the knee to the side of the thigh. By reducing the concentration of force on the bony side of the knee, the wearer would be more comfortable and would have more tolerance for the 3-point pressure being applied to the leg. This would also reduce the potential for skin irritation that sometimes occurs when someone first begins wearing of an osteoarthritis brace.

While preferred embodiments of the invention have been described above, those of ordinary skill in the art will recognize the existence other embodiments and variations so that the invention should not be viewed as limited to the specific embodiments and features shown and described herein

What is claimed is:

1. In a knee brace of the type having a pair of depending opposed femoral links connected by a rigid cross brace, each of said femoral links terminating in a lower end portion, a pair of opposed upwardly extending tibial links connected by a rigid cross brace, each of said tibial links terminating in an upper end portion, a mechanical joint connecting the upper end of one of the tibial links to the lower end of a respective one of the femoral links at each of medial and lateral sides of the knee brace, at least one strap for fixing the brace on a thigh of a leg of a wearer and at least one strap for fixing the brace on the calf of the leg of the wearer, the improvement comprising:

a semi-pliable insert affixed to an inner side of each of the femoral links at two points of fixation with a bottom portion of the semi-pliable insert affixed to one or both of the femoral links being left free to move inward toward a facing side of the leg, the free bottom portion extending downward along the femoral link toward the knee, and at least one strap that is tightenable by the wearer, the at least one strap being attached to one of the semi pliable inserts in a manner enabling pulling on the strap to cause the free bottom portion of the insert to dynamically move inward and compress against the thigh so as to diffuse and transfer pressure away from a relatively boney side of the knee of the wearer to a softer thigh area of the wearer.

2. In a knee brace according to claim 1, wherein said at least one strap comprises anterior and posterior straps that are tightenable by the wearer, the straps being attached to the semi pliable inserts in a manner enabling pulling on the straps to cause the inserts to dynamically move inward and compress against the thigh so as to diffuse and transfer pressure away from a relatively boney side of the knee of the wearer to a softer thigh area of the wearer.

3. In a knee brace according to claim 2, wherein the straps are independently tightened by the wearer.

4. In a knee brace according to claim 3, wherein said two points of fixation comprise a first point of fixation at a top end area of each of the inserts, and second point of fixation approximately at a middle area each of the inserts.

5. In a knee brace according to claim 4, wherein the anterior strap has a point of origin and attachment on one of the inserts and stretches across a front of the thigh and through a loop or slot of the other of the inserts, and wherein the posterior strap has a point of origin and attachment on one of the inserts and stretches across a back side of the thigh and through a loop or slot of the other of the inserts.

6. In a knee brace according to claim 5, wherein compressible pads are attached to an interior side of each the semi-pliable inserts to minimize skin irritation and discomfort when the straps are tightened and said pads being adapted to move inward and press into femoral hollows just proximal to the knee joint of the wearer so as to provide support against movement of the brace along the length of the leg of the wearer.

7. In a knee brace according to claim 6, wherein the knee brace is an osteoarthritis knee brace.

8. In a knee brace according to claim 2, wherein the anterior strap has a point of origin and attachment on one of the inserts and stretches across a front of the thigh and through a loop or slot of the other of the inserts, and wherein the posterior strap has a point of origin and attachment on one of the inserts and stretches across a back side of the thigh and through a loop or slot of the other of the inserts.

9. In a knee brace according to claim 1, wherein the cantilevered portion of the inserts is generally hook-shaped.

10. In a knee brace according to claim 9, wherein the anterior strap has a point of origin and attachment on one of the inserts and stretches across a front of the thigh and through a loop or slot of the other of the inserts, and wherein the posterior strap has a point of origin and attachment on one of the inserts and stretches across a back side of the thigh and through a loop or slot of the other of the inserts.

11. In a knee brace according to claim 10, wherein the knee brace is an osteoarthritis knee brace.

12. In a knee brace according to claim 1, wherein said two points of fixation comprise a first point of fixation at a top end area each of the inserts, and second point of fixation approximately at a middle area each of the inserts.

13. In a knee brace according to claim 1, wherein compressible pads are attached to an interior side of one or more of the semi-pliable inserts to prevent and skin irritation or discomfort when the straps are tightened and said pads being adapted to move inward and press into femoral hollows just proximal to the knee joint of the wearer so as to provide support against movement of the brace along the length of the leg of the wearer.

14. In a knee brace according to claim 1, wherein the knee brace is an osteoarthritis knee brace.

15. In a knee brace according to claim 1, wherein a semi-rigid wedge that tapers upwardly is inserted between the femoral links and each semi-pliable insert.

16. In a knee brace according to claim 1, wherein a spring plate is provided with means for axially contracting the plate so as to cause the spring plate to bow inward toward the leg of the wearer is disposed between at least one of the femoral links and a corresponding one of the semi rigid semi-pliable inserts.

17. In a knee brace according to claim 1, wherein the knee brace is a ligament functional instability knee brace, and wherein the inserts are of the same length, being sized to compress into soft tissue of the femoral hollow above the knee.

* * * * *